US006776159B2

United States Patent
Pelerossi et al.

(10) Patent No.: US 6,776,159 B2
(45) Date of Patent: Aug. 17, 2004

(54) POSITIVE EXPIRATORY PRESSURE DEVICE WITH BYPASS

(75) Inventors: Richard K. Pelerossi, Rome, NY (US); Gregory S. King, Cazenovia, NY (US); Jennifer M. Foran, Bridgeport, NY (US); Lawrence A. Weinstein, Chesterfield, VA (US); Fredrick M. Richards, Clinton, NY (US); Christopher T. Zirps, Sharon, MA (US); Robert H. Elden, Cambridge, MA (US)

(73) Assignee: DHD Healthcare Corporation, Wampsville, NY (US)

( * ) Notice: Subject to any disclaimer, the term of this patent is extended or adjusted under 35 U.S.C. 154(b) by 22 days.

(21) Appl. No.: 10/337,002

(22) Filed: Jan. 3, 2003

(65) Prior Publication Data

US 2003/0127092 A1 Jul. 10, 2003

Related U.S. Application Data

(63) Continuation-in-part of application No. 09/449,208, filed on Nov. 24, 1999.

(51) Int. Cl.$^7$ .............................................. A61M 16/00
(52) U.S. Cl. ............................ 128/204.18; 128/204.19; 128/205.24; 128/205.23
(58) Field of Search ....................... 128/204.18, 204.19, 128/205.24, 205.23; 482/13; 137/908; 600/540, 538

(56) References Cited

U.S. PATENT DOCUMENTS

| | | | |
|---|---|---|---|
| 2,918,917 A | 12/1959 | Emerson | 128/204.21 |
| 3,710,780 A | 1/1973 | Milch | 128/26 R |
| 3,933,171 A * | 1/1976 | Hay | 137/493.7 |
| 4,207,884 A * | 6/1980 | Isaacson | 128/200.24 |
| 4,221,381 A | 9/1980 | Ericson | 272/99 |
| 4,245,633 A * | 1/1981 | Erceg | 128/205.17 |
| 4,257,453 A * | 3/1981 | Kohnke | 137/514.3 |
| 4,327,740 A | 5/1982 | Shuman | 128/728 |
| 4,601,465 A | 7/1986 | Roy | 272/99 |
| 4,611,591 A | 9/1986 | Inui et al. | 128/204.21 |
| 4,644,947 A * | 2/1987 | Whitwam et al. | 128/204.25 |
| 4,651,731 A | 3/1987 | Vicenzi et al. | 128/204.25 |
| RE32,553 E * | 12/1987 | Bennett et al. | 137/271 |
| 4,739,987 A | 4/1988 | Nicholson | 272/99 |
| 4,973,047 A | 11/1990 | Norell | 272/99 |
| 5,018,517 A | 5/1991 | Liardet | |
| 5,020,532 A * | 6/1991 | Mahoney et al. | 128/205.24 |
| 5,027,809 A | 7/1991 | Robinson | 128/203.24 |
| 5,065,746 A | 11/1991 | Steen | 128/204.18 |
| 5,067,707 A | 11/1991 | Kohnke | 272/99 |
| 5,193,529 A | 3/1993 | Labaere | 128/200.24 |
| 5,413,110 A * | 5/1995 | Cummings et al. | 600/508 |
| 5,439,430 A | 8/1995 | Rubens et al. | 482/13 |
| 5,451,190 A | 9/1995 | Liardet | 482/13 |
| 5,540,220 A | 7/1996 | Gropper et al. | 128/204.21 |

(List continued on next page.)

Primary Examiner—Henry Bennett
Assistant Examiner—Mital Patel
(74) Attorney, Agent, or Firm—August E. Roehrig, Jr.; Hancock & Estabrook

(57) ABSTRACT

An oscillatory positive expiratory pressure respiratory therapy device which may be incorporated into the expiratory limb of a ventilator circuit. Accordingly, this device allows a patient on a ventilator to be subjected to positive expiratory pressure (PEP) therapy combined with airway oscillation and intermittent air flow acceleration while allowing the oscillatory PEP respiratory therapy treatment to be bypassed without interrupting the integrity of the ventilating circuit once the device has been installed in the ventilator circuit. In this manner, all expiratory air in the ventilator circuit is accounted for, the expiratory air volume may be accurately monitored and the ventilator circuit does not have to be broken for insertion or removal of the device.

16 Claims, 7 Drawing Sheets

U.S. PATENT DOCUMENTS

| | | | | |
|---|---|---|---|---|
| 5,547,440 A | | 8/1996 | Rubens et al. | 482/13 |
| 5,598,839 A | * | 2/1997 | Niles et al. | 128/205.23 |
| 5,632,298 A | | 5/1997 | Artinian | 137/102 |
| 5,658,221 A | | 8/1997 | Hougen | 482/13 |
| 5,791,339 A | | 8/1998 | Winter | 128/202.22 |
| 5,890,998 A | | 4/1999 | Hougen | 482/13 |
| 5,899,832 A | | 5/1999 | Hougen | 482/13 |
| 5,910,071 A | | 6/1999 | Hougen | 482/13 |
| 5,918,597 A | * | 7/1999 | Jones et al. | 128/205.18 |
| 5,931,159 A | * | 8/1999 | Suzuki et al. | 128/204.18 |
| 6,058,932 A | | 5/2000 | Hughes | 128/200.24 |
| 6,083,141 A | | 7/2000 | Hougen | 482/13 |
| 6,095,139 A | * | 8/2000 | Psaros | 128/204.22 |
| 6,102,038 A | | 8/2000 | DeVries | 128/204.23 |
| 6,581,598 B1 | * | 6/2003 | Foran et al. | 128/204.23 |

* cited by examiner

POSITIVE EXPIRATORY PRESSURE DEVICE WITH BYPASS

This application is a continuation in part of application Ser. No. 09/449,208 filed Nov. 24, 1999.

BACKGROUND OF THE INVENTION

1. Field of the Invention

This invention relates in general to a single patient use, positive oscillatory expiratory pressure respiratory therapy device which includes an air-flow bypass and, in particular, to a positive oscillatory expiratory pressure respiratory therapy device for incorporation into the expiratory limb of a ventilator circuit, and operable by a patient through passive exhalation during the expiratory cycle. The device when in an "on" or "active" mode of operation imposes an oscillatory expiratory air pressure on the patient during exhalation for the purpose of loosening secretions, and in the "off" or "bypass" mode of operation permits free flow of air through the device with minimal or no pressure drop.

2. Description of Related Art

Persons who suffer from pulmonary problems that result in large amounts of mucus being produced in the lungs often require assistance in the removal of these secretions. If these secretions are allowed to remain in the lungs, airway obstruction occurs resulting in poor oxygenation and possible pneumonia and/or death. One of the clinically recognized treatments for this condition is a technique known as positive expiratory pressure therapy or PEP. With PEP therapy, a patient exhales against a resistance to generate expiratory pressure at a substantially constant rate of flow. Prescribed expiratory pressures are generally in the range of 10–20 cm of $H_2O$, although other pressure ranges and pressures can be used.

In the use of PEP therapy, a patient breaths through an orifice restricter to generate a positive pressure in the lungs during exhalation, with the pressure falling to zero at the end of the exhalation. By selection of the proper-sized orifice, a given pressure is determined for the exhalation flow rate generated by an individual patient. This extended, substantially constant, flow of elevated-pressure exhalation has been shown to be effective for moving secretions trapped in the lungs to the larger airways where the secretions can then be removed through coughing. It has also been found that in the treatment of patients having chronic obstructive pulmonary disease (COPD), chronic bronchitis, cystic fibrosis, atelectasis, or other conditions producing retained secretions, treatment with PEP therapy is improved by combining positive expiratory pressure therapy with airway oscillation and intermittent air-flow acceleration. To this end a hand-held, single patient use, positive expiratory pressure respiratory therapy device was developed by assignees of the present invention, and is the subject matter of a co-pending application, Ser. No. 09/449,208, filed Nov. 24, 1999 for "POSITIVE EXPIRATORY PRESSURE DEVICE".

The present invention comprises a positive oscillatory expiratory pressure respiratory therapy device which is incorporated into the expiratory limb of a ventilator circuit. Accordingly, this device allows a patient on a ventilator to be subjected to positive expiratory pressure therapy combined with airway oscillation and intermittent air flow acceleration while allowing this respiratory therapy treatment to be bypassed without interruption once the ventilator circuit has been established. In this manner, all expiratory air in the ventilator circuit is accounted for, and the expiratory air volume may be accurately monitored.

As is known to respiratory therapy healthcare providers, the volume of expiratory air in a ventilator circuit is closely monitored. Once this invention has been installed into the expiratory limb of the ventilator circuit, the ventilator circuit never needs to be broken enabling the healthcare provider to accurately account for all expiratory air and maintain the integrity of the ventilator circuit. In addition, the device is constructed such that any condensation forming in the device will drain out from the housing because of the interior design which facilitates the flow of condensate out from the device into the ventilator circuit. Furthermore, the transparency of the housing permits inspection of the interior to insure that condensate is not being retained in the device.

As is also known to respiratory healthcare providers, the use of an oscillatory expiratory pressure imposed on the patient must be carefully controlled. To this end, a ventilator circuit includes apparatus to closely monitor the positive end expiratory pressure (PEEP). Accordingly, the amount of expiratory air pressure buildup in the opening pressure cycle for producing the airway oscillation, and intermittent air flow acceleration, must be carefully controlled. To this end, during the "on" cycle or "active" mode of operation, the present invention is designed such that oscillatory expiration occurs throughout the entire expiratory air cycle until the expiratory air pressure decreases to the point where oscillation can no longer occur, but never exceeds the allowable PEEP.

SUMMARY OF THE INVENTION

The present invention is directed to overcoming one or more of the problems or disadvantages associated with the relevant technology. As will be more readily understood and fully appreciated from the following detailed description of a preferred embodiment, the present invention is embodied in a positive oscillatory expiratory pressure respiratory therapy device for incorporation into a ventilator circuit. The device includes a bypass for selectively directing the expiratory air discharged from a patient through the device for oscillatory PEP treatment or bypassing the device to discharge the patient's expiratory air directly through the ventilator circuit. In this manner, once the device is installed into a ventilator circuit, the integrity of the ventilator circuit always remains intact and the patient expiratory air volume may be accurately monitored.

DESCRIPTION OF THE DRAWINGS

Further objectives of the invention, together with additional features contributing thereto and advantages accruing therefrom, will be apparent from the following description of a preferred embodiment of the invention which is shown in the accompanying drawings with like reference numerals indicating corresponding parts throughout, wherein.

DETAILED DESCRIPTION OF THE INVENTION

Figure 1:
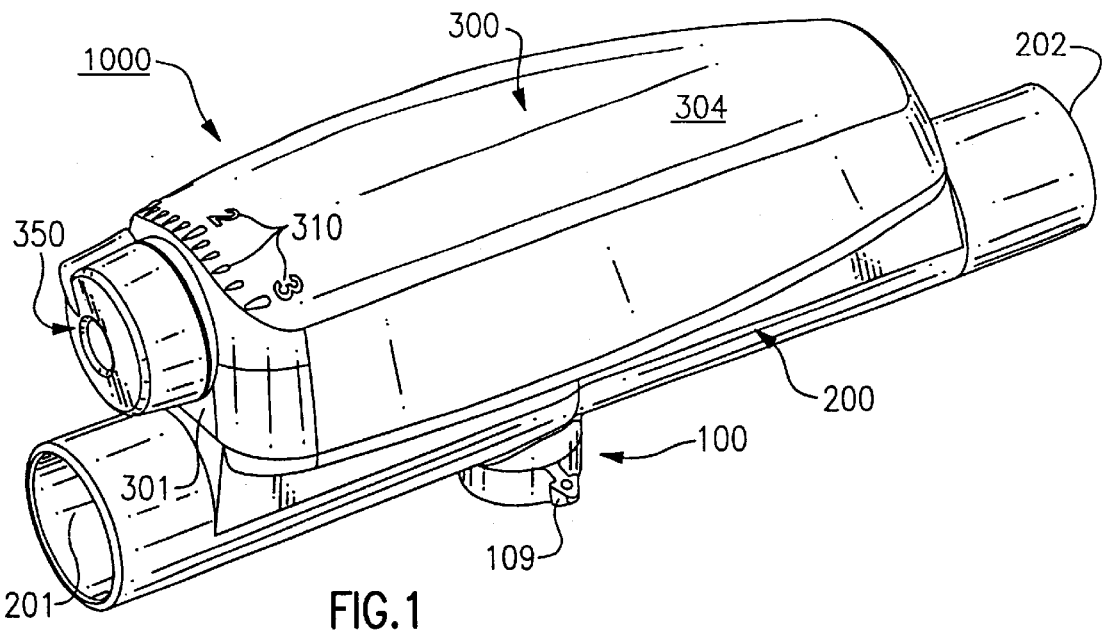
FIG. 1 is a perspective view of the assembled invention.
Figure 2:
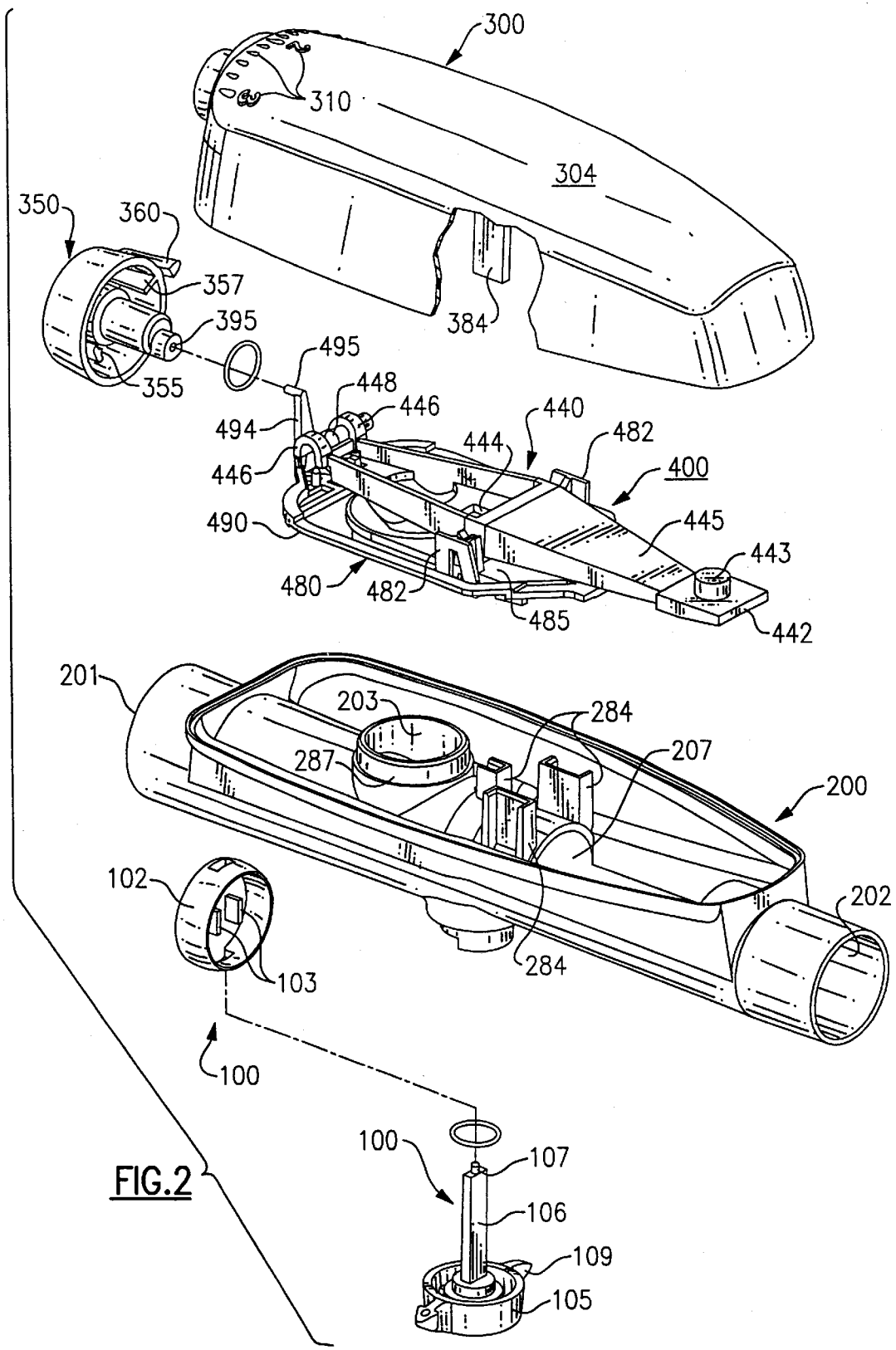
FIG. 2 is an exploded perspective view of the invention with portions removed to better illustrate the internal structure thereof.

Referring now to the drawings, there is illustrated in FIGS. 1 and 2 an oscillatory positive expiratory pressure (PEP) respiratory therapy device 1000 which may be incorporated into the expiratory limb of a ventilator circuit for applying oscillatory positive expiratory air pressure (PEP) therapy to a patient, or for bypassing the oscillatory PEP treatment by coupling the expiratory air flow directly to the remainder of the ventilator circuit.

The oscillatory PEP device 1000 is selectively actuated between two modes of operation, an "on" or "active" mode in which oscillatory PEP therapy is applied, and an "off" or "bypass" mode in which the expiratory air bypasses the therapy applying portion of the device, by operation of an air-flow control valve 100. The air-flow control valve 100 is carried within an air-flow tube 200 and is manually positionable to selectively control the passage of expiratory air through either the oscillatory PEP inducing portion or to bypass that portion of the device.

When the air-flow control valve 100 is in a closed position, blocking free through-flow of the expiratory air, the "on" or "active" mode of the device 1000, expiratory air is passed to and through an upper housing portion 300 of the device 1000 in which is enclosed an expiratory-air-driven oscillatory rocker assembly 400. The expiratory-air-driven oscillatory rocker assembly 400 comprises two portions, a rocker portion 440 and a rocker support or platform portion 480 which act together in creating the oscillatory PEP therapy and are best illustrated in FIGS. 2–9. The details of the structure and operation of this oscillatory PEP portion of the device will be described in detail hereinafter.

To control the magnitude and frequency of the oscillatory pressure applied to a patient, a rotatable frequency control dial 350 is positioned at and carried by one end of the housing 301 in which the rocker assembly 400 is contained. By operation of the adjustable frequency control dial 350 in a manner to be hereinafter described, the relative positioning between the oscillatory PEP inducing portions of the oscillatory rocker assembly 400, the rocker portion 440 and the rocker support portion 480, are adjusted to control the magnitude and frequency of the oscillatory expiratory air pressure.

Figure 3:
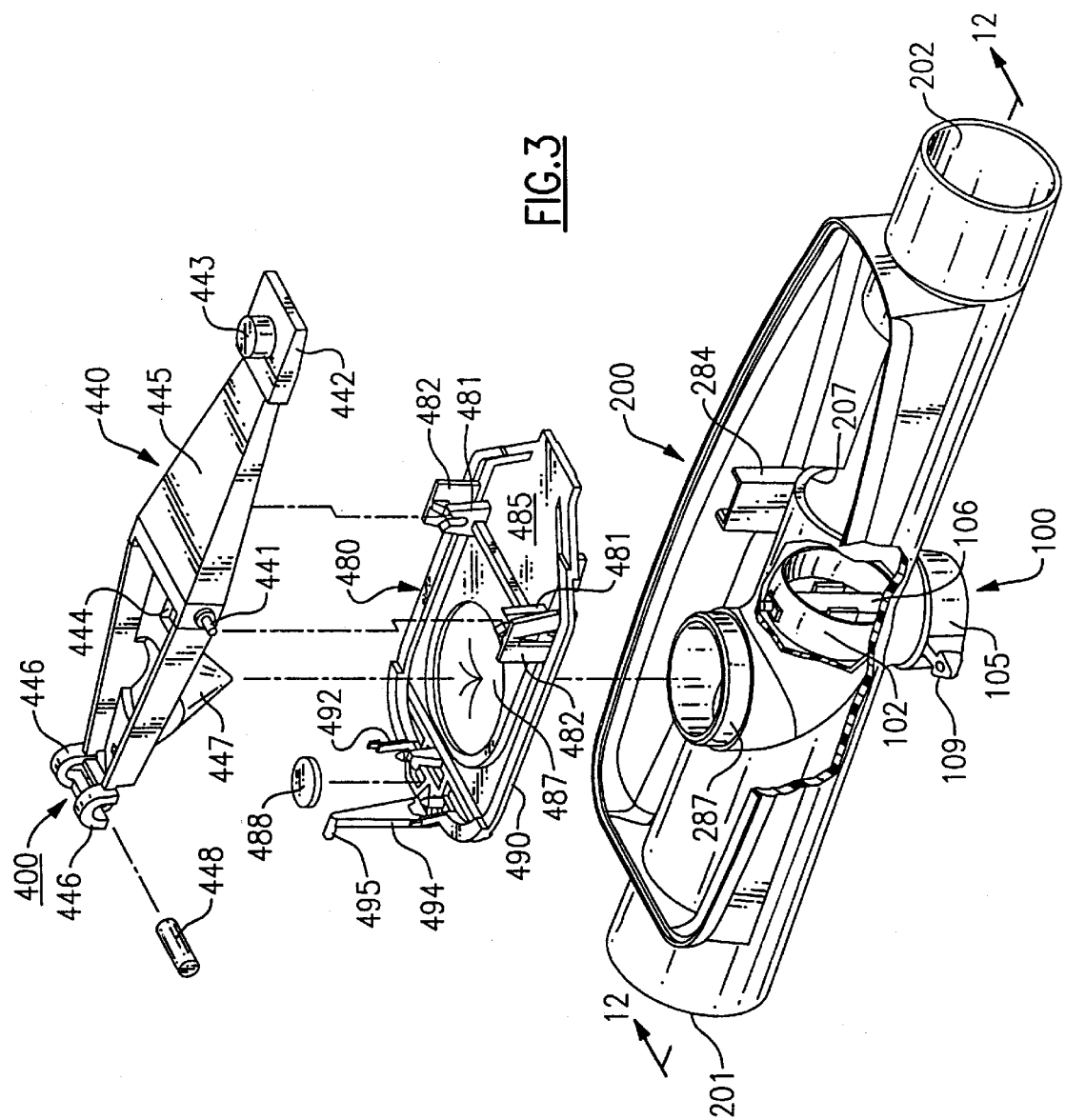
FIG. 3 is an exploded perspective view of the rocker and platform portions of the invention to better illustrate the manner in which a user produces an oscillatory positive expiratory pressure and the manner in which the magnitude and frequency of the oscillations can be adjusted.
Figure 6:
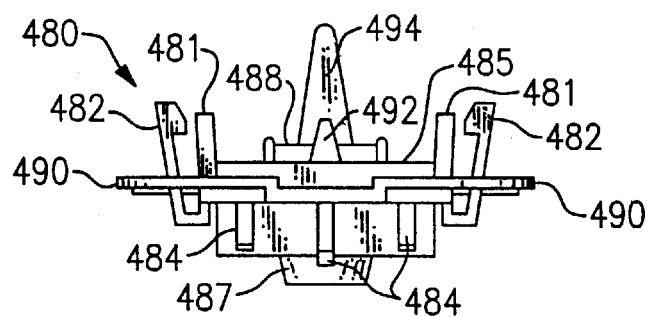
Figure 7:
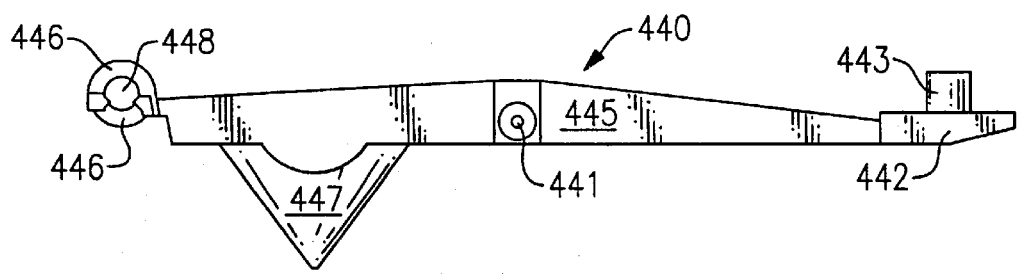
FIGS. 7, 8 and 9 are, respectively, a side profile, top elevation and front profile view of the rocker portion of the invention with portions broken away to show the internal structure which is used in combination with the platform structure of FIGS. 4–6 form the non-linear discharge orifice and create the oscillatory expiratory air pressure.
Figure 8:
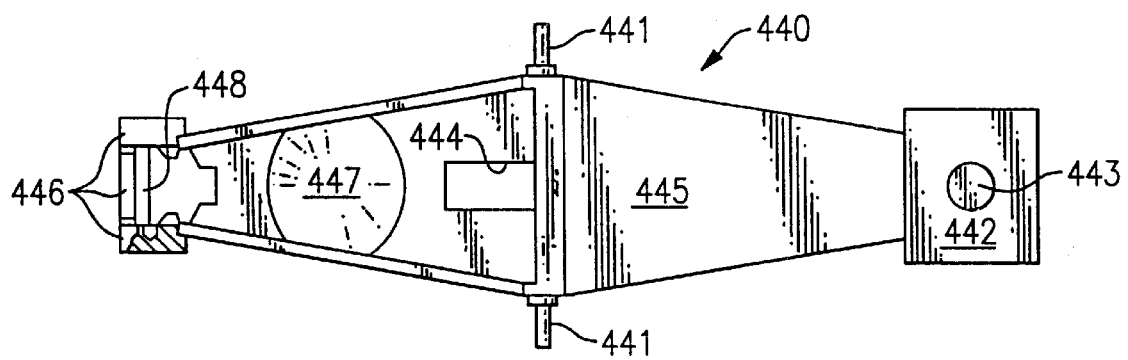
Figure 9:
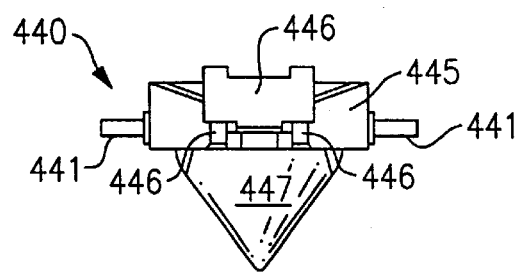

The expiratory-air-driven oscillatory rocker portion 440 is best illustrated in the exploded view of FIG. 3, and in more detail, in FIGS. 7–9. The rocker support portion 480, which functions in cooperation with the rocker portion 440 to produce an oscillatory expiratory air flow and pressure, is also illustrated in the exploded view of FIG. 3, and in more detail in FIGS. 4 through 6. The expiratory-air-driven oscillatory rocker portion 440 and the rocker support portion 480, when assembled together, form the rocker assembly 400.

The rocker assembly 400 is supported on the air-flow tube 200 and carried within the upper housing 300 which forms a sealed chamber with the air-flow tube 200. In this manner, the rocker assembly 400 functions to create an oscillatory positive expiratory air pressure and flow rate in response to a patient's exhalation when the air-flow control valve 100 is closed, the "on" or "active" mode of operation, and the patient's expiratory air is thereby directed to and through the rocker assembly 400.

Figure 12:
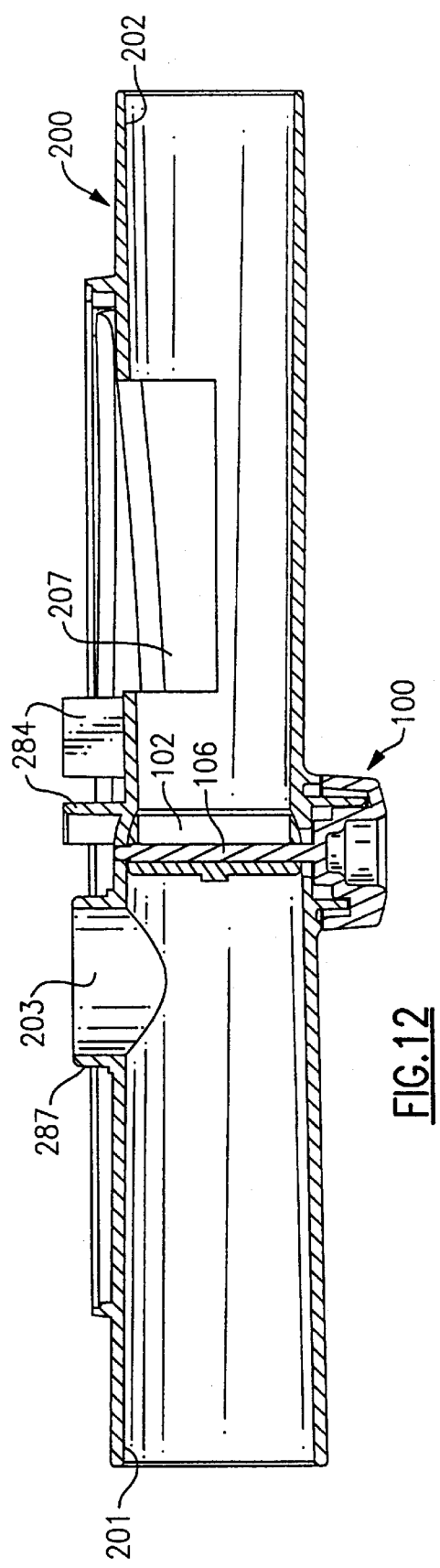
FIG. 12 is a cross-sectional view of the flow tube portion of the invention taken along the lines 12—12 of FIG. 3.
Figure 13:
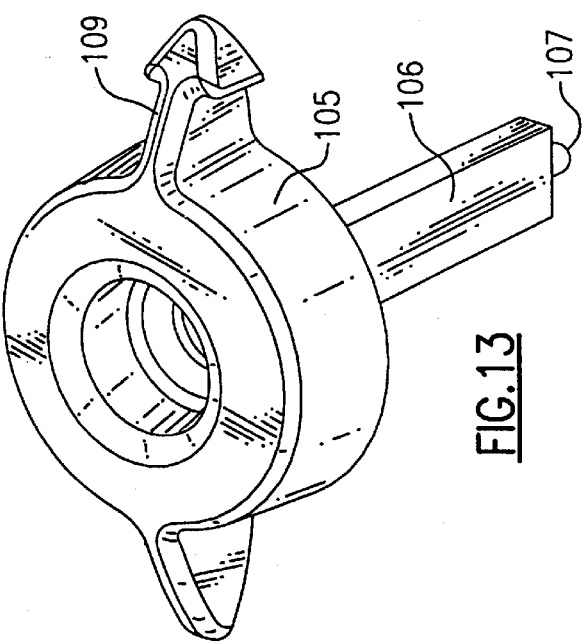
FIG. 13 is an enlarged perspective view of the knob and stem portion of an air-flow control valve, the operation of which selectively controls the air flow movement through the air-flow tube between the oscillatory pressure portion or bypass portion of the invention.

As best shown in FIGS. 3 and 12, there is illustrated the air flow tube 200 having a first or input end 201 for attachment into the expiratory air limb of a ventilator circuit, and a second or output end 202 through which expiratory air passes to the remainder of the expiratory leg of the ventilator circuit. The input and output ends 201 and 202, respectively, are sized as standard female and male fittings so that the air flow tube 200 can be used with tubing of standard size used in a ventilator circuit, frequently 22 mm i.d. and 22 mm o.d. The air flow tube 200 has an opening 203 in the top portion thereof through which expiratory air will be passed to the oscillatory rocker assembly 400 for creating the oscillatory PEP therapy for the patient in a manner to be hereinafter described in detail. To this end, the air flow tube 200 carries the air-flow control valve 100 within the interior of the air flow tube 200 whereby the air-flow control valve 100 is operable between a closed position, wherein the air flow is directed into the housing 300 and through the rocker assembly 400 during the "on" or "active" mode of operation, and an open position, the "off" or bypass mode of operation, whereby the oscillatory PEP therapy is bypassed and the expiratory air is discharged through the remaining portion of the expiratory leg of the ventilator circuit. The selective rotational movement of the air-flow control valve 100 is effected by an air-flow control valve knob 105 extending outwardly from the bottom of the air flow tube 200.

As best illustrated in FIGS. 2, 3, 12 and 13, the air-flow control valve 100 has a tapered circular portion 102 which is carried within the air-flow tube 200 to be rotated between an "on" position blocking the through flow of air through the air-flow tube 200, as illustrated in FIG. 12, and an "off" portion wherein the tapered circular portion 102 is rotated 90° to permit the free flow of air through air-flow tube 200. These two positions correspond, respectively, to the "active" and "bypass" modes of operation.

Rotational movement of the air-flow valve 200 between "on" and "off" positions is effected by turning a knob 105 connected to the tapered circular portion 102. As best illustrated in FIGS. 2, 3, 12, and 13 knob 105 includes a stem 106 which extends through the air-flow tube 200 and the tapered circular portion 102 between guides 103 formed thereon. The distal or terminal end of the stem 106 includes a tip 107 which engages with a suitable recess in the air-flow tube 200 to permit the knob 105, and thereby the tapered circular portion 102, to be rotated between the "on" position blocking the through-flow of air through the air-flow tube 200 and an "off" position permitting the free through-flow of air through the air-flow tube 200. An arrow-shaped indicator 109 is formed on the knob 105 to permit the visual confirmation of the "on" and "off" modes of operation. The air-flow control valve 100 is sized to conform to the cross-sectional shape of the air-flow tube 200 and is rotatable between the closed and open positions to control the "on" and "off" modes of the oscillatory PEP treatment, respectively.

When the air-flow control valve 100 is positioned for operation of the device in the "on" or "active" mode of operation, air flow passing directly through the air-flow tube 200 is blocked, and an air flow path is created which extends from the inlet 201 of the air-flow tube 200 out through the opening 203 in the air-flow tube into the housing 300 to be applied to the oscillatory rocker assembly 400 for creating the oscillatory PEP therapy applied to the patient.

Figure 4:
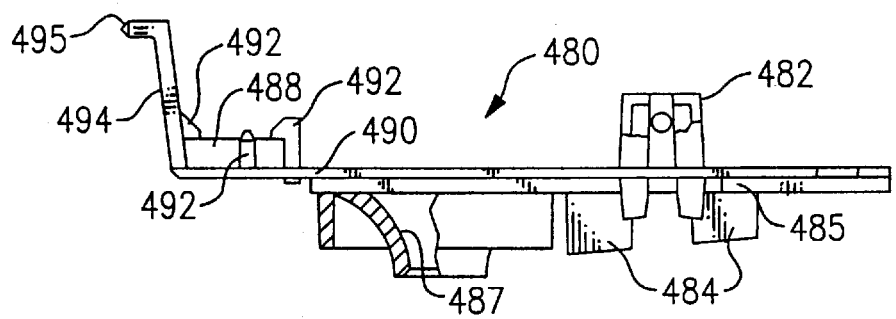
FIGS. 4, 5 and 6 are, respectively, a side profile, top elevation and front profile view of the platform portion of the invention to illustrate a portion of the structure forming the non-linear orifice and a portion of the structure for adjusting the magnitude and frequency of the oscillatory expiratory air pressure.
Figure 5:
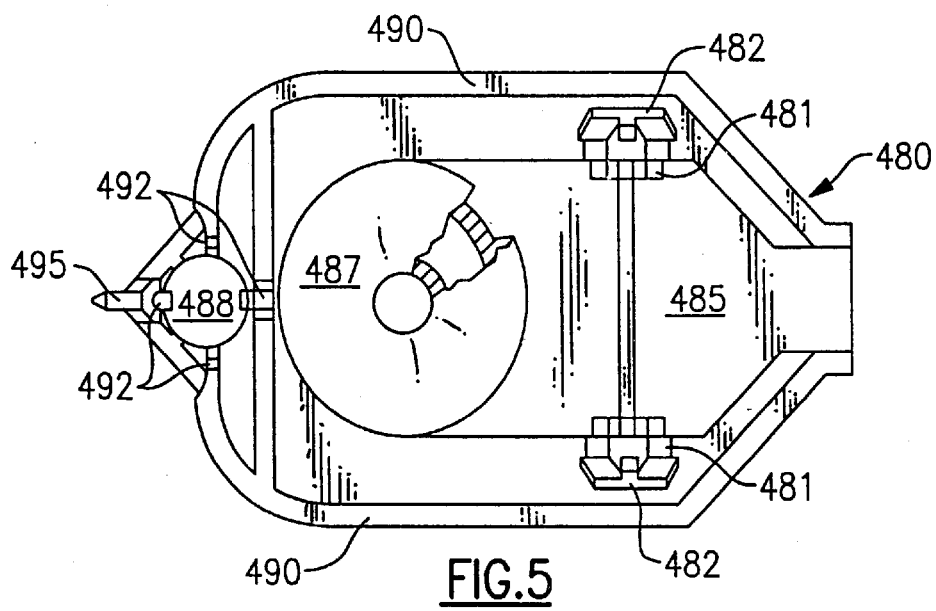

As best illustrated in FIGS. 2–9, the rocker portion 440 is balanced for pivotal movement about pivot pins 441 on spaced pivot supports 481 formed on a platform 485 of the rocker support portion 480. The pivot pins 441 form a transverse pivot axis for the rocker portion 440 which lies in a plane above and extends transverse to the longitudinal axis of the platform 485. The pivot pins 441 are limited in their axial and vertical movement by a pair of locking guides 482, carried by the platform 485 and one of which is positioned adjacent each of the pivot supports 481 to maintain the pivot pins 441 in their proper position on the pivot supports 481. In this manner the rocker portion 440 is pivotal relative to the rocker support portion 480 regardless of the orientation of the device 1000, allowing the oscillatory PEP device 1000 to function regardless of its orientation in use. A balance pad 442 and balancing cylinder 443 are formed at one end of a rocker 445 to balance the weight of a cone-shaped air-flow closure member 447 and a pin of magnetically attractable material, such as a steel pin 448 both of which are carried at the opposite end of the rocker 445. The pin 448 is carried at the distal end of the rocker 445 by a plurality of gripping fingers 446 which partially encircle the pin 448 for holding the pin in a position to be exposed to the magnetic field of a magnet 488 carried on the platform 485. The air-flow closure cone 447 is sized and positioned on the rocker 445 to be periodically inserted into a tapered bell-shaped or trumpet-shaped air-discharge outlet 487 formed in the platform 485 to create the oscillatory PEP when expiratory air is discharged through the opening 203 in the air-flow tube 200 into the housing 300. As best illustrated in FIGS. 3 and 4, the interior of the air-discharge outlet 487 has a non-linear taper or bell-shaped interior surface to form a non-linear air discharge outlet for creating the oscillatory PEP therapy in response to the pivotal movement of the rocker cone 447 in to and out therefrom. In this manner the discharge outlet 487 is periodically closed and re-opened allowing the expiratory air discharged there through to be returned to the air-flow tube 200 at a position downstream of the closed air-flow control valve 100. Accordingly, all of the expiratory air passed into the oscillatory PEP device 1000 when operating in the "on" or "active" mode will be returned to the ventilator circuit through the discharge outlet 207 passing out and thereby through the air-flow tube discharge outlet end 202.

The oscillatory rocker assembly 400 is secured on the air-flow tube 200 and positioned within the housing 300 by means of a plurality of positioning tangs 484 which extend downwardly from the platform 485 and are best illustrated in FIGS. 4 and 6. These tangs 484 are secured in channels 284 extending upwardly from the top of the air-flow tube 200 to securely position the oscillatory rocker assembly 400 onto the air-flow tube 200. In this manner the non-linear tapered, bell-shaped discharge outlet 487 carried by the platform 485 aligns with a cowling 287 of the complementary opening 203 in the air-flow tube 200 into, and through which, the bell-shaped discharge outlet 487 extends. Another tang 384 extends downwardly from the interior of upper portion 304 of the housing 300 and passes through an aperture 444 in the rocker 445 to press downwardly against the platform 485 thereby securing the oscillatory rocker assembly 400 in the proper position on the air-flow tube 200 when the housing 300 is secured thereto.

Figure 10:
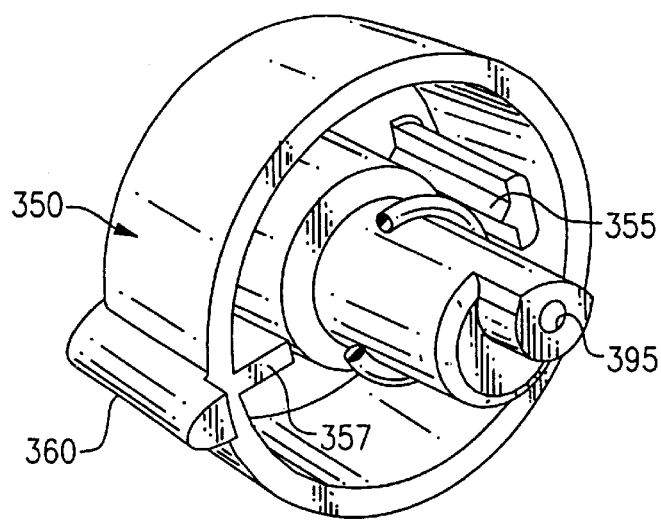
FIG. 10 is a perspective view of an adjustment dial portion of the invention to better illustrate the manner in which the platform portion illustrated in FIGS. 4–6 is positionable relative to the rocker portion illustrated in FIGS. 7–9 to determine the movement of the rocker portion for controlling the oscillatory frequency and pressure.

To create the periodically interrupted discharge of expiratory air for applying the oscillatory PEP therapy to a patient, the magnetically attractable material or steel pin 448 is carried on the pivotal rocker 445 at a position in operative proximity to the magnet 488 carried by the rocker support portion 480. The magnet 488 is carried in a magnet support pocket formed by a plurality of gripping or centering fingers 492. The magnet support pocket is formed at the free end of a vertically positionable U-shaped carrier 490 which is cantilevered from the platform 485. In this manner, the magnet is positioned in proximity to the steel pin 448 to apply a preselected magnetic attraction force thereto. To this end the U-shaped carrier 490 has a vertical positioning link 494 extending vertically upward from a position adjacent to the magnet support pocket 491 and terminating at a distal end in a tip 495 which engages a recess 395 in the oscillation frequency control dial 350. Rotation of the frequency control dial 350 controls the frequency of the oscillations by which the PEP treatment or therapy is applied in accordance with the desires of the healthcare provider. The recess 395 is offset from the center of rotation of the frequency control dial 350 (best illustrated in FIG. 10) such that rotation of the dial 350 will raise or lower the tip 495, engaged therein, thereby moving the magnet 488 towards or away from the steel pin 448 to vary the magnetic attractive force there between.

While the device 1000 will function to provide an oscillatory PEP pulse without the use of the magnetic field between the magnet 488 and the steel pin 448 because of the opening and closing of the tapered non-linear discharge outlet 487 due to the movement of the tapered cone-shaped air-flow closure 447 induced in response to the patient's discharge of expiratory air, the use of the magnetic field permits the device 1000 to provide an adjustable range in the pressure of the patient's expiratory air discharge required to create the oscillatory positive expiratory pressure pulses. By using the magnetic field attraction, the patient's expiratory air pressure required to create the oscillations can be controlled to insure that the positive end expiratory pressure (PEEP) level set by the ventilator circuit is not exceeded. In addition, the magnetic field attraction permits the device 1000 to be operated in any spatial orientation.

Figure 11:
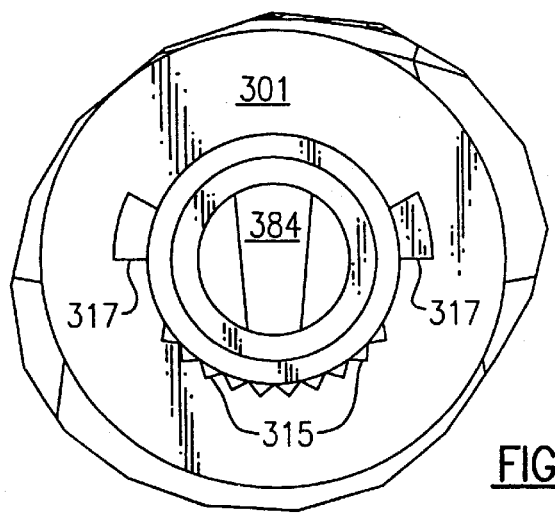
FIG. 11 is an enlarged view of an end portion of the upper housing of the invention to better illustrate the manner in which the movement of the adjustment dial illustrated in FIG. 10 is controlled.

To assist a patient or the healthcare provider in using the device 1000 once the proper magnetic field has been set, a plurality of indicia 310 are spaced along the top of the housing 300. These indicia 310, in combination with a base reference point 360 on the frequency adjusting dial 350, are used to ensure that the correct setting is being maintained after the healthcare provider has established the desired level for treatment. To minimize the occurrence of the rotatable adjusting dial 350 being unknowingly rotated, a series of tooth-like projections 315 are formed on the face of the housing 300 (best seen in FIG. 11) which engage with a mating tooth 355 formed on the interior of the rotatable frequency adjusting dial 350 to provide resistance to movement and an audible sound when the dial 350 is rotated. A pair of stops 317 are formed on the front of the housing 300 which, in combination with a stop 357 formed on the interior of the frequency adjusting dial 350, limit the rotational movement of the dial 350 relative to the housing 300.

INDUSTRIAL APPLICABILITY

Figure 15:
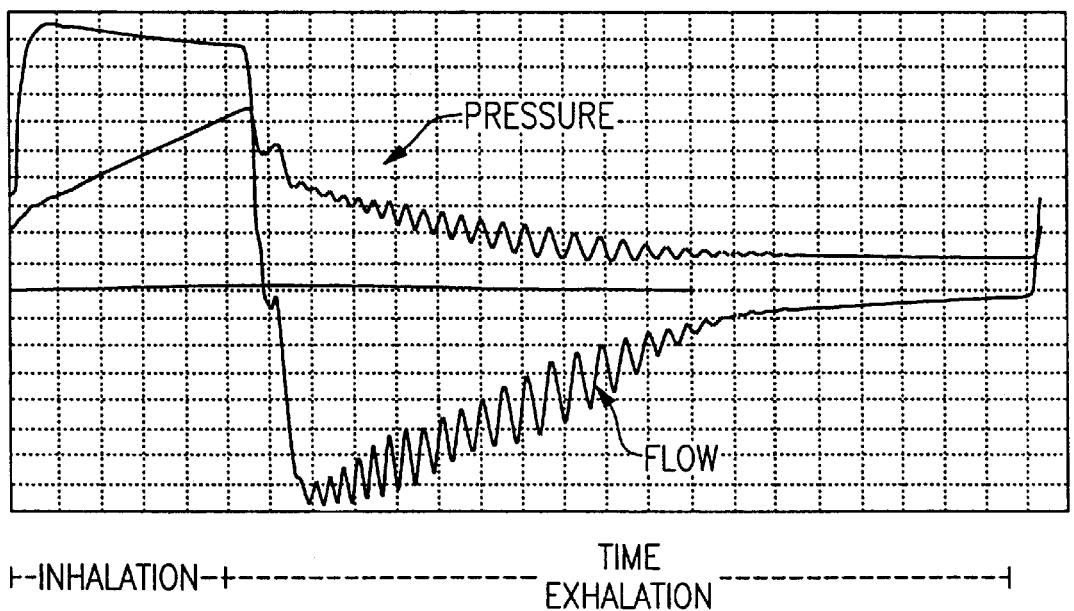
FIG. 15 is a graphical representation of the operation of the invention in the "on" or "active" mode.

During use of the variable frequency or oscillatory PEP device 1000 in a ventilator circuit in the "active" mode, the air-flow control valve 100 is closed and a patient's expiratory air is delivered through the input end 201 of the air-flow tube 200 and passes through the opening 203 to the oscillatory rocker assembly 400. Accordingly, the expiratory air pressure is applied against the cone-shaped closure 447 of the rocker assembly 400 which forms a closure of the non-linear discharge opening or orifice 487. The pressure of the patient's expiratory air will raise the cone-shaped closure 447, causing the rocker portion 440 to pivot about the pivot pins 441 against the force of the magnetic field between the magnet 488 carried on the pivotal rocker support portion 480 and the steel pin 448 carried on the rocker assembly 400. As the cone-shaped closure 447 moves upwardly in response to the increasing expiratory air pressure, the constant taper of the conical shape in conjunction with the bell-shaped non-linear taper of the non-linear discharge opening or orifice 487 increases the effective discharge area thereby decreasing the air pressure applied against the cone-shaped closure 447 and reducing the upward acceleration of the rocker arm 445. When the magnetic force and the Coanda effect of the air flow over the bell-shaped or non-linear tapered interior of the discharge outlet 487 overcome the expiratory air pressure applied to the tapered cone-shaped closure 447, the closure 447 will again begin to move downwardly and accelerate into the bell-shaped non-linear-tapered discharge orifice 487. As the cone descends into the air flow path through the discharge outlet or orifice 487, the annular flow area diminishes reducing the airflow rate and increasing the air pressure. This continues until the downward momentum is overcome and the cone 447 resumes its upward acceleration. Maximum pressure is obtained at this point and another cycle begins. The oscillatory air pressure and air flow during an inhalation and an exhalation cycle when the device is in the "on" or "active" mode of operation is illustrated in the graph of FIG. 15.

Figure 14:
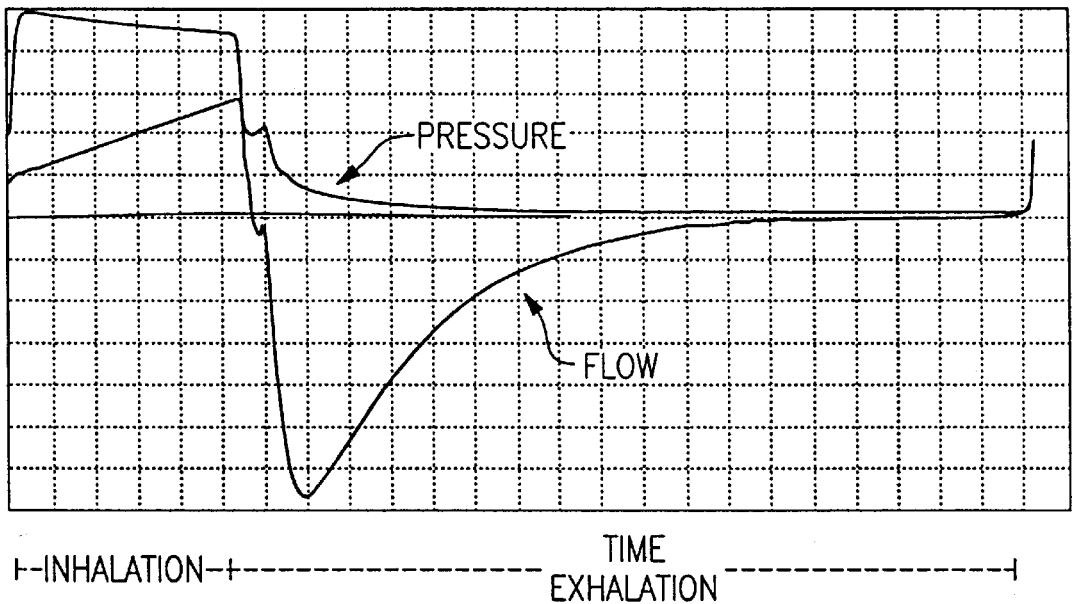
FIG. 14 is a graphical representation of the operation of a ventilator circuit with the invention in the "off" or "bypass" mode.

Positioning the air-flow control valve 100 in an open position, the "off" or "bypass" mode of operation, permits the expiratory air discharged by the patient to bypass the oscillatory rocker assembly 400 and flow directly through the device 1000 and into the rest of the ventilator circuit with no perceptible drop in air pressure because of the substantially unrestricted flow of air through the air-flow tube. Accordingly, once the device 1000 has been installed into the ventilator circuit, it never needs to be removed greatly facilitating the monitoring of the volume of air circulated through the ventilating circuit. The device 1000 will then operate in a passive state allowing the patient to breath in a manner by which the device 1000 will not effect the operation of the ventilator circuit. The passive air pressure and flow rate during an inhalation and exhalation cycle when the device 1000 is in the bypass mode of operation is illustrated in the graph of FIG. 14.

While this invention has been described in the specification and illustrated in the drawings with reference to a preferred embodiment, the structure of which has been disclosed herein, it will be understood by those skilled in the art to which this invention pertains that various changes may be made and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention nor confined to the details set forth, but that the invention will include all embodiments modifications and changes as may come within the scope of the following claims:

What is claimed is:

1. An oscillatory positive expiratory pressure therapy device for installation in a ventilator circuit to induce an oscillatory positive air pressure exhalation by a user, or to bypass the therapy without opening the ventilator circuit in which the device has been installed, comprising:

an air-flow tube having an inlet opening adapted to be connected into a ventilator circuit for receiving expiratory air passed there through by a user receiving respiratory therapy or care, and an outlet opening adapted to be connected into the ventilator circuit for discharging the expiratory air passed through said inlet opening;

air-flow control means carried within said air-flow tube for directing the flow of expiratory air received through said inlet opening in a first path of air movement for inducing a respiratory treatment in the user or in a second path of air movement bypassing the respiratory treatment;

said air-flow tube including expiratory air responsive closure means positioned in said first path of air movement and actuable between an open position and a closed position in response to the pressure of expiratory air passed thereto; and said expiratory air responsive closure means including a normally closed non-linear discharge outlet which is opened in response to the presence of a predetermined pressure of expiratory air being passed in said first path of air movement, and which closes in response to a predetermined rate of air pressure decrease through said non-linear discharge opening.

2. The oscillatory positive expiratory pressure therapy device of claim 1 wherein said expiratory air responsive closure means includes a cone-shaped closure member pivotally movable in response to expiratory air pressure between a closed position blocking the flow of expiratory air in said first path of air movement and an open position permitting the flow of expiratory air in said first path of air movement.

3. The oscillatory positive expiratory pressure therapy device of claim 1 wherein said non-linear discharge outlet positioned in said first path of air movement comprises a non-linear tapered discharge orifice.

4. The oscillatory positive expiratory pressure therapy device of claim 1 wherein said non-linear discharge outlet positioned in said first path of air movement comprises a bell-shaped discharge orifice.

5. The oscillatory positive expiratory pressure therapy device of claim 1 wherein said non-linear discharge outlet positioned in said first path of air movement comprises a trumpet-shaped air discharge outlet.

6. The oscillatory positive expiratory pressure therapy device of claim 1 further including a magnetic force field applying means for generating a biasing force effecting the opening and closing of said non-linear discharge opening.

7. The oscillatory positive expiratory pressure therapy device of claim 6 further including means for adjusting the magnitude of the magnetic force field applying means to bias the opening and closing of said non-linear discharge opening.

8. The oscillatory positive expiratory pressure therapy device of claim 7 wherein said means for adjusting the magnitude of the magnetic force field applying means includes a rotatable frequency control dial.

9. The oscillatory positive expiratory pressure therapy device of claim 8 wherein said rotatable frequency control dial includes a receiving aperture operatively connected to said expiratory air responsive closure means for adjusting the expiratory air pressure for opening said non-linear discharge opening.

10. The oscillatory positive expiratory pressure therapy device of claim 1 wherein said expiratory air responsive closure means positioned in said first path of air movement and actuable between an open position and a closed position in response to the pressure of expiratory air passed thereto comprises an oscillatory rocker assembly including a rocker portion pivotally supported on a rocker support portion.

11. The oscillatory positive expiratory pressure therapy device of claim 10 wherein said rocker portion includes a cone-shaped closure member carried on said rocker portion for pivotal movement into and out from said non-linear discharge opening; and said rocker support portion includes a bell-shaped non-linear discharge orifice which is opened and closed in response to the movement of said cone-shaped closure member.

12. A method of selectively effecting oscillatory positive expiratory pressure therapy in a patient using a ventilator circuit without interruption of the circuit integrity, comprising:

passing a flow of patient-induced expiratory air from a ventilator circuit into an air-flow tube having an air-flow control valve for selectively passing the expiratory air in a first path of air movement for inducing oscillatory positive expiratory pressure therapy and in a second path of air movement bypassing said oscillatory positive expiratory pressure therapy;

blocking a discharge opening for expiratory air moving in said first path of air movement and thereby increasing the expiratory air pressure as said expiratory air continues in said first path of air movement;

opening said discharge opening in response to the increase of the expiratory air pressure to a predetermined level, and then reducing the expiratory air pressure at a variable rate by passing the discharge of expiratory air through a non-linear discharge orifice to induce an oscillatory positive expiratory pressure in the patient; and actuating said air-flow control valve to selectively pass said flow of expiratory air from said first path of air movement for inducing oscillatory positive pressure therapy to said second path of air movement for bypassing said oscillatory positive expiratory pressure therapy when said oscillatory positive expiratory pressure therapy has been completed to return said flow of expiratory air through said air-flow tube to the ventilator circuit.

13. The method of selectively effecting oscillatory positive expiratory pressure therapy of claim 12 wherein the steps of blocking the discharge opening for expiratory air moving in said first path of air movement and thereby increasing the expiratory air pressure as said expiratory air continues to flow in said first path of air movement, and opening said discharge opening in response to the increase of the expiratory air pressure to a predetermined level and then reducing the expiratory air pressure at a variable rate bypassing the discharge of expiratory air through a non-linear discharge orifice to induce an oscillatory positive expiratory pressure in the patient are repeated until a sufficient oscillatory positive expiratory pressure therapy has been effected.

14. The method of selectively effecting oscillatory positive expiratory pressure therapy of claim 12 further including applying a biasing force for closing said discharge opening to control the predetermined level of expiratory air pressure.

15. The method of selectively effecting oscillatory positive expiratory pressure therapy of claim 14 wherein said biasing force is a magnetic force field.

16. The method of selectively effecting oscillatory positive expiratory pressure therapy of claim 12 wherein said step of reducing the expiratory air pressure at a variable rate by passing the discharge of expiratory air through a non-linear discharge orifice includes application of the Coanda effect.

* * * * *